US008193322B2

(12) United States Patent
Yan et al.

(10) Patent No.: US 8,193,322 B2
(45) Date of Patent: Jun. 5, 2012

(54) METHODS FOR GENERATING MONOVALENT IGG

(75) Inventors: Wei Yan, Sammamish, WA (US); Michael Wittekind, Bainbridge Island, WA (US); Carla Forte, Bainbridge Island, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/585,505

(22) Filed: Oct. 23, 2006

(65) Prior Publication Data

US 2007/0105199 A1  May 10, 2007

Related U.S. Application Data

(60) Provisional application No. 60/729,304, filed on Oct. 21, 2005.

(51) Int. Cl.
  *C07K 16/46* (2006.01)
  *C12P 21/08* (2006.01)
(52) U.S. Cl. .................. 530/388.22; 530/391.1
(58) Field of Classification Search ............... 530/388.2, 530/391.1
See application file for complete search history.

(56) References Cited

U.S. PATENT DOCUMENTS

| | | | |
|---|---|---|---|
| 4,925,673 | A | 5/1990 | Steiner et al. |
| 5,013,556 | A | 5/1991 | Woodle et al. |
| 5,284,656 | A | 2/1994 | Platz et al. |
| 5,677,425 | A | 10/1997 | Bodmer et al. |
| RE35,862 | E | 7/1998 | Steiner et al. |
| 5,792,451 | A | 8/1998 | Sarubbi et al. |
| 5,807,706 | A | 9/1998 | Carter et al. |
| 6,121,022 | A | 9/2000 | Presta et al. |
| 6,468,529 | B1 | 10/2002 | Schwall et al. |
| 6,833,441 | B2 | 12/2004 | Wang et al. |
| 2002/0142374 | A1 | 10/2002 | Gallo et al. |
| 2003/0078385 | A1 | 4/2003 | Arathoon et al. |
| 2003/0157091 | A1 | 8/2003 | Hoogenboom |
| 2006/0276633 | A1* | 12/2006 | Jung et al. ............ 530/387.1 |

FOREIGN PATENT DOCUMENTS

| | | |
|---|---|---|
| WO | WO 96/27011 | 9/1996 |
| WO | WO 96/32478 A1 | 10/1996 |
| WO | WO 97/34631 | 9/1997 |
| WO | WO 97/34631 A1 | 9/1997 |
| WO | WO 02/056910 A1 | 7/2002 |
| WO | WO 2004/058820 A2 | 7/2004 |
| WO | WO 2004/058820 A3 | 7/2004 |
| WO | WO 2005/000899 A2 | 1/2005 |
| WO | WO 2005/000899 A3 | 1/2005 |
| WO | WO 2005/063816 A2 | 7/2005 |
| WO | WO 2005/063816 A3 | 7/2005 |

OTHER PUBLICATIONS

Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
MacCallum et al. (J. Mol. Biol. (1996) 262:732-745).*
Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Salfeld (Nature Biotech. 25(12): 1369-1372 (2007).*
Lederman et al (Molecular Immunology 28:1171-1181, 1991).*
Li et al (Proc. Natl. Acad. Sci. USA 77:3211-3214, 1980).*
Dall'Acqua (J. Immunol. 177:1129-1138 (2006)).*
Ibragimova and Eade (Biophysical Journal, Oct. 1999, vol. 77, pp. 2191-2198).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987)).*
Lin et al Biochemistry USA vol. 14:1559-1563 (1975)).*
Abuchowski, et al., "13. Soluble Polymer-Enzyme Adducts," in Enzymes as Drugs, Hocenberg and Roberts, eds., Wiley-Interscience, New York, New York pp. 367-383 (1981).
Adjei, et al., "Bioavailability of leuprolide following intratracheal administration to beagle dogs," *Int. J. Pharm.* 61:135-144 (1990).
Adjei and Garren, "Pulmonary delivery of peptide drugs: effect of particle size on bioavailability of leuprolide acetate in healthy male volunteers," *Pharm. Res.* 7:565-569 (1990).
Braquet et al., "Effect of endothelin-1 on blood pressure and bronchopulmonary system of the guinea pig," *J. Cardiovasc. Pharmacol.*, 13(Suppl. 5):S143-146 (1989).
Brocks et al., "A TNF receptor antagonistic scFv, which is not secreted in mammalian cells, is expressed as a soluble mono- and bivalent scFv derivative in insect cells," *Immunotechnology* 3:173-184 (1997).
Burton, "Immunoglobulin G: functional sites," *Mol. Immunol.* 22:161-206 (1985).
Carter, "Bispecific human IgG by design," *J Immunol Methods* 248:7-15 (2001).
Debs et al., "Lung-specific delivery of cytokines induces sustained pulmonary and systemic immunomodulation in rats," *J. Immunol.*, 140:3482-3488 (1988).
Dechend et al., "AT1 receptor agonistic antibodies, hypertension, and preeclampsia," *Semin. Nephrol.* 24:571-579 (2004).
Devereux et al., "A comprehensive set of sequence analysis programs for the VAX," *Nucleic Acids Res.* 12:387-395 (1984).
Ellison et al., "The nucleotide sequence of a human immunoglobulin $C_{\gamma 1}$ gene," *Nucleic Acids Res.* 10:4071-4079 (1982).
Glickman et al., "Androstenedione may organize or activate sex-reversed traits in female spotted hyenas," *Proc. Natl. Acad. Sci. USA* 84:3444-3447 (1987).

(Continued)

Primary Examiner — Lynn Bristol
(74) Attorney, Agent, or Firm — Rosemary Sweeney

(57) ABSTRACT

The present invention relates to monovalent antibody, methods of making thereof and therapeutic uses thereof. In particular, the present invention provides a heterodimeric polypeptide comprising an immunoglobulin heavy chain and a fusion protein comprising an immunoglobulin light chain and an Fc molecule.

40 Claims, 6 Drawing Sheets

OTHER PUBLICATIONS

Gribskov and Burgess, "Sigma factors from *E. coli*, *B. subtilis*, phage SP01, and phage T4 are homologous proteins," *Nucleic Acids Res.* 14:6745-6763 (1986).

Hogarth, "Fc receptors are major mediators of antibody based inflammation in autoimmunity," *Curr. Opin. Immunol.* 14:798-802 (2002).

Holliger and Hudson, "Engineered antibody fragments and the rise of single domains," *Nat. Biotechnol.* 23(9):1126-1136 (2005).

Hubbard et al., "Anti-neutrophil-elastase defenses of the lower respiratory tract in α1-Antitrypsin deficiency directly augmented with an aerosol of α1-Antitrypsin," *Ann. Intern Med.* 111:206-212 (1989).

Junghans, "*Finally*! The Brambell Receptor (FcRB)," *Immunol. Res.* 16:29-57 (1997).

Larrick et al., "Polymerase chain reaction using mixed primers: cloning of human monoclonal antibody variable region genes from single hybridoma cells," *Biotechnology* 7:934-938 (1989).

Leong et al., "Adapting pharmacokinetic properties of a humanized anti-interleukin-8 antibody for therapeutic applications using site-specific pegylation," *Cytokine* 16:106-119 (2001).

Li et al., "Activation of integrin αIIβ3 by modulation of transmembrane helix associations," *Science* 300:795-798 (2003).

Locksley et al., "The TNF and TNF receptor superfamilies: integrating mammalian biology," *Cell* 104:487-501 (2001).

Marshall, "Chapter 10. Solid oral dosage forms," in Modern Pharmaceutics, 1st Ed., Banker, G.S. and Rhodes, C.T., Eds., pp. 359-427 (1979).

Mohler et al., "Soluble tumor necrosis factor (TNF) receptors are effective therapeutic agents in lethal endotoxemia and function simultaneously as both TNF carriers and TNF antagonists," *J. Immunol.* 151:1548-1561 (1993).

Needleman and Wunsch, "A general method applicable to the search for similarities in the amino acid sequence of two proteins," *J. Mol. Biol.* 48:443-453 (1970).

Newmark et al., "Preparation and properties of adducts of streptokinase and streptokinase-plasmin complex with polyethylene glycol and pluronic polyol F38," *J. Appl. Biochem.* 4:185-189 (1982).

Oeswein et al., "Aerosolization of Protein Pharmaceuticals," Proceedings of Symposium on Respiratory Drug Delivery II, pp. 14-49, Keystone, CO, Mar. 1990.

Pin et al., "Allosteric functioning of dimeric class C G-protein-coupled receptors," *FEBS J.* 272:2947-2955 (2005).

Riechmann et al., "Reshaping human antibodies for therapy," *Nature* 332:323-327 (1988).

Rudnic et al., "Chapter 89: Oral Solid Dosage Forms," in Remington's Pharmaceutical Sciences, 18$^{th}$ Ed., pp. 1633-1665, Mack Pub. Co., Easton, PA. (1990).

Schlessinger, "Cell signaling by receptor tyrosine kinases," *Cell* 103:211-225 (2000).

Schwartz and Dayhoff, "23. Matrices for detecting distant relationships," Atlas of Protein Sequence and Structure, National Biomedical Research Foundation, vol. 5. Suppl. 3, pp. 353-358 (1978).

Smith and Waterman, "Comparison of biosequences," *Advances in Applied Mathematics* 2(4):482-489 (1981).

Smith et al., "Pulmonary deposition and clearance of aerosolized Alpha-1-proteinase inhibitor administered to dogs and to sheep," *J. Clin. Invest.* 84:1145-1154 (1989).

Kuby, "Chapter 5: Immunoglobulins: structure and function," *Immunology* 2$^{nd}$ edition, W. H. Freeman and Company, New York, pp. 109-131,1991.

NIH Publication No. 91-3242, "Sequences of proteins of immunological interest," Fifth Edition, Kabat et al., Eds., pp. 1571-1610, 1991.

Weng et al., "Computational determination of the structure of rat Fc bound to the neonatal Fc receptor," *J. Mol. Biol.* 282:217-225, 1998.

Bird and Walker, "Single chain antibody variable regions," *Tibtech* 9:132-137, 1991.

Edelman et al., "The Covalent Structure of an Entire γG Immunoglobulin Molecule," *Biochemistry* 63:78-85, 1969.

NIH Publication No. 91-3242, "Sequences of proteins of immunological interest," Fifth Edition, Kabat et al., Eds., pp. iii-xi, xviii, 2355, 2385, 1991.

Paul, "Chapter 1: The Immune System," *Fundamental Immunology*, Third Edition, Ed. William E. Paul, Raven Press, Ltd., New York, pp. 8-9, 1993.

Snapper and Finkelman, "Chapter 22: Immunoglobulin Class Switching,", *Fundamental Immunology, Third Edition*, Ed. William E. Paul, Raven Press, Ltd., New York, pp. 837-838, 1993.

Carayannopoulos and Capra, Immunoglobulins Structure and Function, Ch. 9, pp. 283-314 at 284-285 *in* Fundamental Immunology, 3$^{rd}$ Edition, Paul, ed., Raven Press, New York, 1993.

Fredericks et al., Identification of potent human anti-IL-IR$_1$ antagonist antibodies, *Protein Engineering, Design & Selection* 17(1): 95-106, 2004.

NIH Publication No. 91-3242, "Sequences of proteins of immunological interest," Fifth Edition, Kabat et al., Eds., pp. 1582, 1587, 1592, 1609-1610, 1991.

Grossman and Turner, "The Mathematics of Counting," *in* Mathematics for the Biological Sciences, Macmillan Publishing Co., Inc., 1974, pp. 17-30.

\* cited by examiner

14D2VH-huCH1-huFc-(His)6

EVQLVESGGGLVQTGKSLELSCEASGFTFSNYDMNWVRQAPGKGLE
WVAYISSGSGHIYYGDAVKGRFTISRDNAKNLLFLQMNNLKSEDTAM
YYCSGSYWFAYWGQGTLVTVSLASTKGPSVFPLAPSSKSTSGGTAAL
GCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIE
KTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVM
HEALHNHYTQKSLSLSPGKHHHHHH (SEQ ID NO: 9)

14D2VL-huKLC-huFc(ΔEPKSC)

DIVMSQSPSSLAVSAGEKVTIGCKSSQSLLNNKDQKNYLNWYQQKPG
QSPKLLIFFASTRHIGVPDRFMGSGSGTDFTLTINSVQNEDLADYYCLQ
TYSFPYTFGAGTKLEIKRTVAAPSVFIFPPSDEQLKSGTASVVCLLNNF
YPREAKVQWKVDNALQSGNSQESVTEQDSKDSTYSLSSTLTLSKADY
EKHKVYACEVTHQGLSSPVTKSFNRGECDKTHTCPPCPAPELLGGPSV
FLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEK
TISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMH
EALHNHYTQKSLSLSPGK (SEQ ID NO: 10)

|-----------FR1--------------|-CDR1|-----FR2------| evqlvesggglvqtgkslelsceasgftfs nydmn wvrqapgkglewva

|------CDR2------|-----------FR3-----------------|-CDR3-| yissgsghiyygdavkg rftisrdnaknllflqmnnlksedtamyycsg sywfay

|---FR4--| wgqgtlvtv

>14D2VL

|---------FR1----------|------CDR1------|------FR2-------| divmsqspsslavsagekvtigc kssqsllnnkdqknyln wyqqkpgqspkllif

|-CDR2-|-------------FR3----------------|--CDR3--| fastrhi gvpdrfmgsgsgtdftltinsvqnedladyyc lqtysfpyt

|--FR4--|

Fgagtkle

Figure 6

SEQUENCE LISTING

```
<160> NUMBER OF SEQ ID NOS: 29

<210> SEQ ID NO 1
<211> LENGTH: 29
<212> TYPE: DNA
<213> ORGANISM: Hamster sp.

<400> SEQUENCE: 1
ctggtgctag cgatatagtg atgtcgcag                                    29

<210> SEQ ID NO 2
<211> LENGTH: 30
<212> TYPE: DNA
<213> ORGANISM: Hamster sp.

<400> SEQUENCE: 2
cagccaccgt acgtttgatt tccagcttgg                                   30

<210> SEQ ID NO 3
<211> LENGTH: 31
<212> TYPE: DNA
<213> ORGANISM: Hamster sp.

<400> SEQUENCE: 3
cgtttaaacg tcgacgttta aacgccgcca g                                 31

<210> SEQ ID NO 4
<211> LENGTH: 35
<212> TYPE: DNA
<213> ORGANISM: Hamster sp.

<400> SEQUENCE: 4
ggcatgtgtg agttttgtca cactctcccc tgttg                             35

<210> SEQ ID NO 5
<211> LENGTH: 35
<212> TYPE: DNA
<213> ORGANISM: Hamster sp.
```

<400> SEQUENCE: 5
caacagggga gagtgtgaca aaactcacac atgcc                    35

<210> SEQ ID NO 6
<211> LENGTH: 31
<212> TYPE: DNA
<213> ORGANISM: Hamster sp.

<400> SEQUENCE: 6
gtttaaacag atccgcggcc gctctagccc c                        31

<210> SEQ ID NO 7
<211> LENGTH: 29
<212> TYPE: DNA
<213> ORGANISM: Hamster sp.

<400> SEQUENCE: 7
gagggcgcgc cgaagtgcag ctggtggag                           29

<210> SEQ ID NO 8
<211> LENGTH: 29
<212> TYPE: DNA
<213> ORGANISM: Hamster sp.

<400> SEQUENCE: 8
ggtgctagct aaagagacgg tgaccagag                           29

<210> SEQ ID NO 9
<211> LENGTH: 451
<212> TYPE: PRT
<213> ORGANISM: Hamster sp.

<400> SEQUENCE: 9

Glu Val Gln Leu Val Glu Ser Gly Gly Gly Leu Val Gln Thr Gly Lys
1               5                   10                  15

Ser Leu Glu Leu Ser Cys Glu Ala Ser Gly Phe Thr Phe Ser Asn Tyr
            20                  25                  30

Asp Met Asn Trp Val Arg Gln Ala Pro Gly Lys Gly Leu Glu Trp Val
        35                  40                  45

Ala Tyr Ile Ser Ser Gly Ser Gly His Ile Tyr Tyr Gly Asp Ala Val
    50                  55                  60

Lys Gly Arg Phe Thr Ile Ser Arg Asp Asn Ala Lys Asn Leu Leu Phe
65                  70                  75                  80

Leu Gln Met Asn Asn Leu Lys Ser Glu Asp Thr Ala Met Tyr Tyr Cys
                85                  90                  95

Ser Gly Ser Tyr Trp Phe Ala Tyr Trp Gly Gln Gly Thr Leu Val Thr
            100                 105                 110

Val Ser Leu Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys

```
                195                 200                 205
Val Asp Lys Arg Val Glu Pro Lys Ser Asp Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys His His His
        435                 440                 445

His His His
    450

<210> SEQ ID NO 10
<211> LENGTH: 447
<212> TYPE: PRT
<213> ORGANISM: Hamster sp.

<400> SEQUENCE: 10

Asp Ile Val Met Ser Gln Ser Pro Ser Ser Leu Ala Val Ser Ala Gly
1               5                   10                  15

Glu Lys Val Thr Ile Gly Cys Lys Ser Ser Gln Ser Leu Leu Asn Asn
            20                  25                  30

Lys Asp Gln Lys Asn Tyr Leu Asn Trp Tyr Gln Gln Lys Pro Gly Gln
        35                  40                  45

Ser Pro Lys Leu Leu Ile Phe Phe Ala Ser Thr Arg His Ile Gly Val
    50                  55                  60

Pro Asp Arg Phe Met Gly Ser Gly Ser Gly Thr Asp Phe Thr Leu Thr
65                  70                  75                  80

Ile Asn Ser Val Gln Asn Glu Asp Leu Ala Asp Tyr Tyr Cys Leu Gln
                85                  90                  95

Thr Tyr Ser Phe Pro Tyr Thr Phe Gly Ala Gly Thr Lys Leu Glu Ile
            100                 105                 110

Lys Arg Thr Val Ala Ala Pro Ser Val Phe Ile Phe Pro Pro Ser Asp
```

```
            115                 120                 125
Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 11
<211> LENGTH: 5
<212> TYPE: PRT
<213> ORGANISM: Hamster sp.

<400> SEQUENCE: 11

Asn Tyr Asp Met Asn
1               5

<210> SEQ ID NO 12
<211> LENGTH: 17
<212> TYPE: PRT
<213> ORGANISM: Hamster sp.

<400> SEQUENCE: 12
```

```
Tyr Ile Ser Ser Gly Ser Gly His Ile Tyr Tyr Gly Asp Ala Val Lys
 1               5                  10                  15
Gly
```

<210> SEQ ID NO 13
<211> LENGTH: 6
<212> TYPE: PRT
<213> ORGANISM: Hamster sp.

<400> SEQUENCE: 13

```
Ser Tyr Trp Phe Ala Tyr
 1               5
```

<210> SEQ ID NO 14
<211> LENGTH: 30
<212> TYPE: PRT
<213> ORGANISM: Hamster sp.

<400> SEQUENCE: 14

```
Glu Val Gln Leu Val Glu Ser Gly Gly Gly Leu Val Gln Thr Gly Lys
 1               5                  10                  15
Ser Leu Glu Leu Ser Cys Glu Ala Ser Gly Phe Thr Phe Ser
            20                  25                  30
```

<210> SEQ ID NO 15
<211> LENGTH: 14
<212> TYPE: PRT
<213> ORGANISM: Hamster sp.

<400> SEQUENCE: 15

```
Trp Val Arg Gln Ala Pro Gly Lys Gly Leu Glu Trp Val Ala
 1               5                  10
```

<210> SEQ ID NO 16
<211> LENGTH: 32
<212> TYPE: PRT
<213> ORGANISM: Hamster sp.

<400> SEQUENCE: 16

```
Arg Phe Thr Ile Ser Arg Asp Asn Ala Lys Asn Leu Leu Phe Leu Gln
 1               5                  10                  15
Met Asn Asn Leu Lys Ser Glu Asp Thr Ala Met Tyr Tyr Cys Ser Gly
            20                  25                  30
```

<210> SEQ ID NO 17
<211> LENGTH: 9
<212> TYPE: PRT
<213> ORGANISM: Hamster sp.

<400> SEQUENCE: 17

```
Trp Gly Gln Gly Thr Leu Val Thr Val
 1               5
```

<210> SEQ ID NO 18
<211> LENGTH: 17
<212> TYPE: PRT
<213> ORGANISM: Hamster sp.

<400> SEQUENCE: 18

```
Lys Ser Ser Gln Ser Leu Leu Asn Asn Lys Asp Gln Lys Asn Tyr Leu
 1               5                  10                  15
Asn
```

```
<210> SEQ ID NO 19
<211> LENGTH: 7
<212> TYPE: PRT
<213> ORGANISM: Hamster sp.

<400> SEQUENCE: 19

Phe Ala Ser Thr Arg His Ile
1               5

<210> SEQ ID NO 20
<211> LENGTH: 9
<212> TYPE: PRT
<213> ORGANISM: Hamster sp.

<400> SEQUENCE: 20

Leu Gln Thr Tyr Ser Phe Pro Tyr Thr
1               5

<210> SEQ ID NO 21
<211> LENGTH: 23
<212> TYPE: PRT
<213> ORGANISM: Hamster sp.

<400> SEQUENCE: 21

Asp Ile Val Met Ser Gln Ser Pro Ser Ser Leu Ala Val Ser Ala Gly
1               5                   10                  15

Glu Lys Val Thr Ile Gly Cys
            20

<210> SEQ ID NO 22
<211> LENGTH: 15
<212> TYPE: PRT
<213> ORGANISM: Hamster sp.

<400> SEQUENCE: 22

Trp Tyr Gln Gln Lys Pro Gly Gln Ser Pro Lys Leu Leu Ile Phe
1               5                   10                  15

<210> SEQ ID NO 23
<211> LENGTH: 32
<212> TYPE: PRT
<213> ORGANISM: Hamster sp.

<400> SEQUENCE: 23

Gly Val Pro Asp Arg Phe Met Gly Ser Gly Ser Gly Thr Asp Phe Thr
1               5                   10                  15

Leu Thr Ile Asn Ser Val Gln Asn Glu Asp Leu Ala Asp Tyr Tyr Cys
            20                  25                  30

<210> SEQ ID NO 24
<211> LENGTH: 8
<212> TYPE: PRT
<213> ORGANISM: Hamster sp.

<400> SEQUENCE: 24

Phe Gly Ala Gly Thr Lys Leu Glu
1               5

<210> SEQ ID NO 25
<211> LENGTH: 29
<212> TYPE: PRT
<213> ORGANISM: Hamster sp.

<400> SEQUENCE: 25
```

```
Gly Ala Gly Gly Gly Cys Gly Cys Gly Cys Cys Gly Ala Ala Gly Thr
1               5                   10                  15

Gly Cys Ala Gly Cys Thr Gly Thr Gly Gly Ala Gly
            20                  25
```

<210> SEQ ID NO 26
<211> LENGTH: 29
<212> TYPE: PRT
<213> ORGANISM: Hamster sp.

<400> SEQUENCE: 26

```
Gly Gly Thr Gly Cys Thr Ala Gly Cys Thr Ala Ala Gly Ala Gly
1               5                   10                  15

Ala Cys Gly Gly Thr Gly Ala Cys Cys Ala Gly Ala Gly
            20                  25
```

<210> SEQ ID NO 27
<211> LENGTH: 113
<212> TYPE: PRT
<213> ORGANISM: Hamster sp.

<400> SEQUENCE: 27

```
Glu Val Gln Leu Val Glu Ser Gly Gly Gly Leu Val Gln Thr Gly Lys
1               5                   10                  15

Ser Leu Glu Leu Ser Cys Glu Ala Ser Gly Phe Thr Phe Ser Asn Tyr
            20                  25                  30

Asp Met Asn Trp Val Arg Gln Ala Pro Gly Lys Gly Leu Glu Trp Val
        35                  40                  45

Ala Tyr Ile Ser Ser Gly Ser Gly His Ile Tyr Tyr Gly Asp Ala Val
    50                  55                  60

Lys Gly Arg Phe Thr Ile Ser Arg Asp Asn Ala Lys Asn Leu Leu Phe
65                  70                  75                  80

Leu Gln Met Asn Asn Leu Lys Ser Glu Asp Thr Ala Met Tyr Tyr Cys
                85                  90                  95

Ser Gly Ser Tyr Trp Phe Ala Tyr Trp Gly Gln Gly Thr Leu Val Thr
            100                 105                 110

Val
```

<210> SEQ ID NO 28
<211> LENGTH: 111
<212> TYPE: PRT
<213> ORGANISM: Hamster sp.

<400> SEQUENCE: 28

```
Asp Ile Val Met Ser Gln Ser Pro Ser Ser Leu Ala Val Ser Ala Gly
1               5                   10                  15

Glu Lys Val Thr Ile Gly Cys Lys Ser Ser Gln Ser Leu Leu Asn Asn
            20                  25                  30

Lys Asp Gln Lys Asn Tyr Leu Asn Trp Tyr Gln Gln Lys Pro Gly Gln
        35                  40                  45

Ser Pro Lys Leu Leu Ile Phe Phe Ala Ser Thr Arg His Ile Gly Val
    50                  55                  60

Pro Asp Arg Phe Met Gly Ser Gly Ser Gly Thr Asp Phe Thr Leu Thr
65                  70                  75                  80

Ile Asn Ser Val Gln Asn Glu Asp Leu Ala Asp Tyr Tyr Cys Leu Gln
                85                  90                  95

Thr Tyr Ser Phe Pro Tyr Thr Phe Gly Ala Gly Thr Lys Leu Glu
            100                 105                 110
```

```
<210> SEQ ID NO 29
<211> LENGTH: 5
<212> TYPE: PRT
<213> ORGANISM: Hamster sp.

<400> SEQUENCE: 29

Glu Pro Lys Ser Cys
1               5
```

METHODS FOR GENERATING MONOVALENT IGG

RELATED APPLICATIONS

This application claims the benefit of U.S. Provisional Application No. 60/729,304, filed Oct. 21, 2005, which is hereby incorporated by reference.

BACKGROUND OF THE INVENTION

Monoclonal antibodies have become an increasingly important class of therapeutic molecules for numerous indications, including cancer, inflammatory diseases and viral infections. By specifically binding to their targets, such as cytokines in circulation or receptors on the cell surface, antibodies can either block or activate certain biochemical steps. In addition, upon binding to their targets, such as foreign organisms or cancer cells, antibodies can also recruit other effector cells from the immune system to the targets, which can lead to the destruction of the targets.

Most recombinant antibodies are used in the IgG format: a "Y"-shaped molecule with two antigen binding fragment (Fab) arms connected to the Fc fragment by a flexible hinge region. The bivalent nature of IgG offers several functional advantages over the monovalent antibody such as Fab. First, by the avidity effect, IgG, which has two antigen binding moieties, binds to its target more tightly than does a monovalent Fab molecule. This typically can be translated into a much higher activity in vivo. Secondly, compared to the Fab fragment, the IgG has a longer serum half-life in mammals, the result of having both a large molecular size, which prevents clearance in the kidneys, and the ability of its Fc region to bind to the neonatal receptor (FcRn) to avoid proteolysis in the endothelium, using a salvage pathway (Junghans, Immunol. Res. 16(1):29-57 (1997)).

In addition, IgG can also mimic the function of a biological ligand by crosslinking the receptors of the ligand on the cell surface. For example, anti-Fas antibodies, similar to Fas ligand (FasL), can activate Fas-mediated apoptosis in many cell types. Another example is anti-CD3 antibody, which is commonly used to activate T cell receptors in vivo (i.e., agonistic antibody). Currently, several agonistic antibodies to the TRAIL receptors are being developed as promising anti-cancer agents as they can induce TRAIL-mediated apoptosis. The biological functions of these agonistic antibodies depend on the bivalency of the IgG format.

The monovalent form of the same antibody, such as Fab fragment, typically fails to work as an agonistic antibody.

For certain therapeutic targets, for example, TNF receptors and the other members of the TNF receptor family, however, the activation of cell surface receptor by antibodies crosslinking is not desirable. TNF receptor family members have been shown to play important roles in many physiological and pathophysiological conditions in human, which make them attractive targets for drug intervention, in particular, by antibody-based therapeutics. However, it is difficult to develop an antibody to the members of the TNF receptor family that is purely antagonistic. The difficulty is mainly due to the potential risk of having an antibody that is both antagonistic and agonistic, in particular for a bivalent antibody such as a full IgG.

Although the monovalent forms of antibody, such as Fab, are free of agonistic activity, it is impractical to be used in vivo due to its short half-life. To overcome this problem, several strategies have been developed in the art, including fusing Fab to large molecules such as serum albumin, and by pegylation of Fab (Leong, S. R., Cytokine, 16(3):106-19 (2001). These approaches, however, are far from being optimal, due to decreased bioactivity and accumulation of PEG molecules in the kidney.

Thus there remains a considerable need for improved methods to develop an antagonistic antibody that has long half-life in vivo but is free of agonistic activity. The present invention fulfills this need by providing a heterodimeric polypeptide which functions as a monovalent antibody.

SUMMARY OF THE INVENTION

The present invention is based, in part, on the observation that monovalent antibody is less likely to be agonistic than a multivalent antibody (e.g., bivalent) such as a full immunoglobulin molecule, which has two antigen-binding domains. The present invention also takes advantage of another observation that in mammalian cells, immunoglobulin heavy chain cannot be secreted from the cells without being dimerized with the light chain.

Accordingly, in one embodiment, the present invention provides a heterodimeric polypeptide comprising an immunoglobulin heavy chain which is linked to a fusion protein, in a covalent or non-covalent interaction, the fusion protein comprising an immunoglobulin light chain and a Fc molecule, wherein the heavy chain and the fusion protein are oriented identically with respect to their N- and C-termini, and wherein the heterodimeric polypeptide is capable of specifically binding to a target receptor. In another aspect, the interaction between the heavy chain and the fusion protein involves a disulfide bond.

In another aspect, the immunoglobulin heavy chain in the heterodimeric polypeptide further comprises a tagging moiety, including but not limited to hexa-histidine (His$_6$) tag, streptavidin-binding peptide, maltose-binding protein, glutathione S-transferase, mic-tag, and FLAG-tag.

In another aspect, the Fc region of the immunoglobulin heavy chain and that of the fusion protein may be mutated to favor or to enhance the interaction between the heavy chain and the fusion protein, including a free-thiol compound such as cysteine and a dimerization domain, in order to more efficiently form the heterodimer polypeptide. In particular, homodimerization of the heavy chain or the fusion protein, respectively, is less favored than the heterodimer formation between them.

In another aspect, the hinge region in the Fc portion of the fusion protein is so modified that the heavy chain and the fusion protein forming the heterodimer are structurally symmetrical to each other. In particular, the hinge region may be modified by amino acid insertion, deletion, or substitution. By such modification, the hinge region may be extended, or shortened by, at least one amino acid residue, by at least two amino acid residues, by at least three amino acid residues, by at least four amino acid residues, by at least five amino acid residues, by at least six amino acid residues, by at least seven amino acid residues, by at least eight amino acid residues, by at least nine amino acid residues, or by at least ten amino acid residues. Furthermore, by such modification, the hinge region may be extended, or shortened by, at least 1-10, 1-11, 1-12, 1-13, 1-14, 1-15, 1-16, 1-17, 1-18, 1-19, or 1-20 amino acid residues, all inclusive, or even longer than shorter, as long as it does not affect the interaction between the heavy chain and the fusion protein and the biological activity of the heterodimeric polypeptide. In another embodiment, at least 1, 2, 3, 4, 5, 6, 7, 8, 9, or 10 amino acid residues in the hinge region may also be substituted with a similar amino acid residue, for example, including but not limited to, substituting a glutamic acid with an aspartic acid, an arginine with a lysine or glutamine, a glutamine with an asparagine. In yet another aspect, the hinge region may be of natural occurrence or non-natural occurrence. The hinge region may comprise a complete hinge region derived from an antibody of a different class or subclass from that of the CH1 domain.

In another embodiment of the present invention, the heterodimeric polypeptide contains no unpaired cysteine, i.e., a cysteine that is not participating in a disulfide bond. It will be appreciated to one skilled in the art to make a heterodimeric polypeptide that has no unpaired cysteines, since the presence of an unpaired cysteine may affect the proper folding and hence the biological activity of the protein.

In another aspect of the present invention, the immunoglobulin heavy chain and the fusion protein in the heterodimeric polypeptide is derived from IgG1, IgG2, IgG3, or IgG4.

In yet another aspect of the present invention, the heterodimeric polypeptide is capable of specifically binding to and antagonizing the activity of a target receptor or cell surface molecule.

In one embodiment of the present invention, the target receptor includes a receptor for which activity is mediated by the oligomerization of its subunits, whether the subunits are of the same (i.e., homo-oligomerization) or different (i.e., hetero-oligomerization) molecules and whether they are dimer, trimer, tetramer, or of higher multimers.

In another embodiment, the target receptor of the heterodimeric polypeptide includes, but is not limited to, TNF/TNF receptor superfamily, cytokine receptors, receptor tyrosine kinases, G-protein coupled receptors (GPCRs), Fc receptors (FcRs), AT1 receptors, tissue factors, and integrins. In yet another embodiment, the target receptor includes a member of the TNF/TNF receptor superfamily, including but not limited to, TNFR1 (p55), TNFR2 (p75), NGFR, Troy, EDAR, XEDAR, CD40, DcR3, Fas, OX40, AITR, CD30, HveA, 4-1BB, DR3, CD27, LTβR, RANK, TWEK receptor, TACI, BCMA, DR6, OPG, DR4, DR5, DcR1 and DcR2.

In another embodiment, the target receptor includes an interleukin receptor, which includes but is not limited to IL-1, IL-2, IL-4, IL-15, IL-7, TSLP, LIF, IL-13, IL-23 and IL-31.

In yet another embodiment of the present invention, the immunoglobulin sequence of the heterodimeric polypeptide is fully human, humanized or chimeric.

In another embodiment, the present invention provides a composition comprising the heterodimeric polypeptide of the present invention and a pharmaceutically acceptable carrier.

In yet another embodiment, the heterodimeric polypeptide of the present invention, or a pharmaceutical composition thereof, is used to treat a subject having a condition mediated by a target receptor which is activated by the oligomerization of its subunits, comprising administering to the subject an effective amount of the heterodimeric polypeptide of the present invention, wherein the heterodimeric polypeptide is capable of specifically binding to at least one subunit of the target receptor thereby antagonizing the oligomerization. In another aspect, this oligomerization forms a dimer, a trimer, or a tetramer, or a complex of higher multimers. In yet another aspect, the present invention provides a heterodimeric polypeptide which targets against at least a member of TNF/TNF receptor superfamily, cytokine receptors, receptor tyrosine kinases, G-protein coupled receptors (GPCRs), Fc receptors (FcRs), AT1 receptors, tissue factors, and integrins. In yet anther aspect, the target receptor includes, but is not limited to, TNFR1, TNFR2, NGFR, Troy, EDAR, XEDAR, CD40, DcR3, Fas, OX40, AITR, CD30, HveA, 4-1BB, DR3, CD27, LTβR, RANK, TWEK receptor, TACI, BCMA, DR6, OPG, DR4, DR5, DcR1 and DcR2. In another aspect of the present invention, the oligomerization of the target receptor may or may not be ligand induced.

In another embodiment, the present invention provides a vector comprising a first nucleic acid encoding an immunoglobulin heavy chain and a second nucleic acid encoding a fusion protein, the fusion protein comprising an immunoglobulin light chain, a hinge region, and a Fc molecule, wherein the first nucleic acid and the second nucleic acid are inserted in the vector at the same or different site(s). In another aspect, the first nucleic acid encodes an immunoglobulin heavy chain which is fused to a tagging moiety.

In another embodiment, the present invention provides a host cell transformed with the vector comprising the first and second nucleic acids as described in the immediately above paragraph.

In yet another aspect, the present invention provides a transformed or transfected host cell comprising at least two vectors, at least one of the vectors comprising a nucleic acid sequence encoding at least an immunoglobulin heavy chain and at least another one of the vectors comprising a nucleic acid sequence encoding at least a fusion protein comprising an immunoglobulin light chain, a hinge region and an Fc molecule.

In another embodiment, the present invention provides a process for producing, in a host cell, a heterodimeric polypeptide, the heterodimeric polypeptide comprising an immunoglobulin heavy chain which is optionally fused to a tagging moiety, the heavy chain is linked to a fusion protein comprising an immunoglobulin light chain, a hinge region, and an Fc molecule, wherein the heavy chain and the fusion protein are oriented identically with respect to their N- and C-termini, and wherein the heterodimeric polypeptide is capable of specifically binding to a target receptor, the process comprising the steps of: (a) transforming or transfecting a host cell with a first nucleic acid encoding the immunoglobulin heavy chain and a second nucleic acid encoding the fusion protein, and (b) expressing the first nucleic acid and the second nucleic acid so that the immunoglobulin heavy chain and the fusion protein are produced separately in the transformed host cell. In another aspect, the heterodimeric polypeptide is expressed in the host cell and secreted therefrom as a heterodimeric polypeptide which is capable of binding to a target receptor. In another aspect, the first and second nucleic acids are present in one single vector or in separate, independent, or different vectors. In yet another aspect, the first nucleic acid may be transformed into a host cell to make the heavy chain, and the fusion protein may be transformed into a separate host cell to make the fusion protein. The host cell transformed with the second nucleic acid may be of the same or different cell or cell line from the host cell transformed with the first nucleic acid. In yet another aspect, the host cell is prokaryotic or eukaryotic. In yet another aspect, the host cell is a mammalian cell, which includes but is not limited to Chinese Hamster Ovarian cells (CHO), VERO, BHK, HeLa, Cos, MDCK, 293, 3T3, a myeloma cell line, and WI38 cells. In yet another embodiment, the heavy chain and the fusion protein are produced in insoluble form and are solubilized and allowed to refold in solution to form a heterodimeric polypeptide which is capable of specifically binding to a target receptor.

In another embodiment, the present invention provides a fusion protein comprising an immunoglobulin light chain fused to an Fc molecule. In another embodiment, the present invention provides a nucleic acid encoding a fusion protein comprising an immunoglobulin light chain fused to an Fc molecule.

In yet another embodiment, the present invention provides a half-molecule of an immunoglobulin, i.e., a two-chain molecule, which comprises a single antigen-binding domain, and in which the light chain is further extended with an Fc molecule that results in a fusion protein. In another aspect, the antigen-binding region comprises at least a CDR1, CDR2, or CDR3 of the heavy and/or the light chain part of the fusion protein.

In yet another embodiment, the present invention provides a polypeptide comprising an immunoglobulin light chain which is fused to an Fc molecule. In another aspect, the light chain is fused to an Fc molecule via a hinge region.

In one embodiment, the present invention provides a heterodimeric polypeptide targeting against TNFR1, comprising a first polypeptide comprising the amino acid sequence set forth in SEQ ID NO:9 and a second polypeptide comprising the amino acid sequence set forth in SEQ ID NO:10. In another aspect, the heterodimeric polypeptide comprises (a) an immunoglobulin heavy chain comprising a CDR of at least 80%, at least 85%, at least 90%, or at least 95% identical to an amino acid sequence selected from the group consisting of: SEQ ID NOS:11, 12, and 13, and (b) a fusion protein comprising an immunoglobulin light chain, a hinge region and a Fc, wherein the light chain comprises a CDR of at least 80%, at least 85%, at least 90%, or at least 95% identical to an amino acid sequence selected from the group consisting of: SEQ ID NOS:18, 19 and 20, and wherein the heterodimeric polypeptide is capable of binding to and antagonizing the activity of TNFR1.

In yet another embodiment, the present invention provides a nucleic acid encoding a polypeptide comprising the amino acid sequence set forth in SEQ ID NO:10.

In yet another embodiment, the present invention provides a nucleic acid encoding polypeptide comprising the amino acid sequence set forth in SEQ ID NO:10.

In yet another embodiment, the present invention provides a nucleic acid encoding an immunoglobulin heavy chain comprising a CDR of at least 80%, at least 85%, at least 90%, or at least 95% identical to an amino acid sequence selected from the group consisting of: SEQ ID NOS:11, 12 and 13, and/or a fusion protein comprising an immunoglobulin light chain, a hinge region and a Fc, wherein the light chain comprises a CDR of at least 80%, at least 85%, at least 90%, or at least 95% identical to an amino acid sequence selected from the group consisting of: SEQ ID NOS:18, 19 and 20.

In yet another embodiment, the present invention provides a method of treating a subject having an autoimmune disease, comprising administering to the subject an effective amount of a heterodimeric polypeptide, or a pharmaceutical composition thereof, which comprises a first polypeptide comprising the amino acid sequence set forth in SEQ ID NO:9 and a second polypeptide comprising the amino acid sequence set forth in SEQ ID NO:10. In another aspect, the present invention provides a method of treating a subject having an autoimmune disease, including but not limited to rheumatoid arthritis, psoriasis, multiple sclerosis, Crohn's disease, IBD, ulcer colitis, comprising administering to the subject an effective amount of a heterodimeric polypeptide, or a pharmaceutical composition thereof, which comprises (a) an immunoglobulin heavy chain comprising a CDR of at least 80%, at least 85%, at least 90%, or at least 95% identical to an amino acid sequence selected from the group consisting of: SEQ ID NOS:11, 12 and 13, and (b) a fusion protein comprising an immunoglobulin light chain, a hinge region and a Fc, wherein the light chain comprises a CDR of at least 80%, at least 85%, at least 90%, or at least 95% identical to an amino acid sequence selected from the group consisting of: SEQ ID NOS:18, 19 and 20, and wherein the heterodimeric polypeptide is capable of binding to and antagonizing the activity of TNFR1.

BRIEF DESCRIPTION OF THE DRAWINGS

FIG. 5 shows the amino acid sequences of a monovalent antibody directed against p55, 14D2, as described in the Examples: the heavy chain which is tagged with His6 (upper) and the fusion protein comprising the light chain fused to an Fc monomer (lower).

FIG. 6 shows the variable sequences of the heavy chain (upper)(SEQ ID NO:27) and light chain (lower)(SEQ ID NO:28) of a monoclonal antibody directed against p55, 14D2. The locations and the sequences of the CDRs (Complementary Domain Region) and FRs (Framework Region) in each variable domain are as indicated.

DETAILED DESCRIPTION OF THE INVENTION

Figure 1:
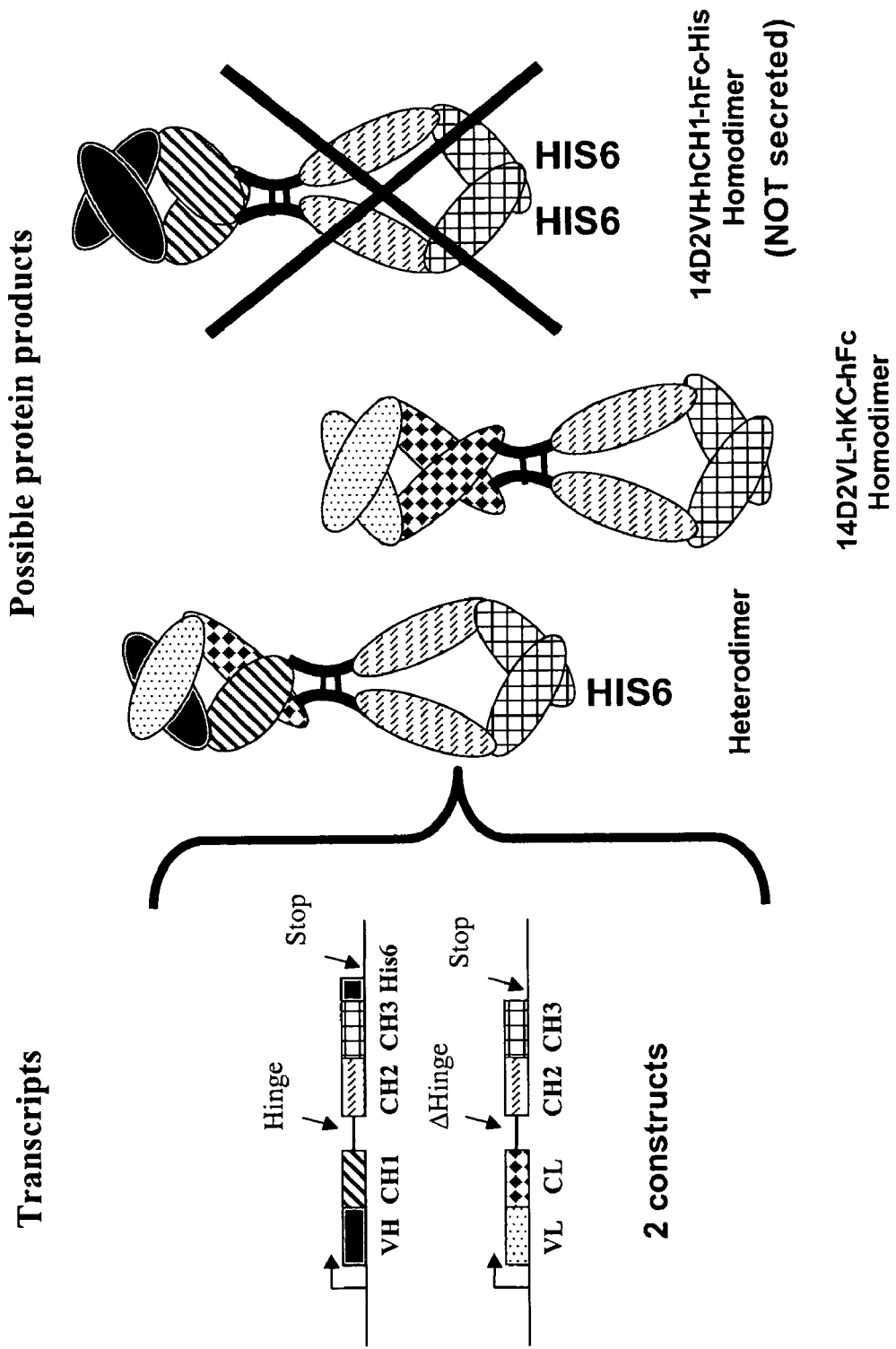
FIG. 1 illustrates a design of a two-chain monovalent IgG. Illustrated on the left are two mammalian expression constructs, one encoding the heavy chain (top) and the other (bottom), a fusion protein comprising the light chain fused to an Fc molecule. The heavy chain and the light chain are from an anti-mouse p55TNFR monovalent IgG designated as 14D2. The three possible protein products are diagramed on the right. As indicated, the heavy chain homodimer cannot be secreted. ΔHinge is the same as Hinge except the first five amino acids (EPKSC)(SEQ ID NO:29) are deleted.

Throughout this disclosure, various publications, patents and published patent applications are referenced by an identifying citation. The disclosures of these publications, patents and published patent applications are hereby incorporated by reference into the present disclosure.

General Techniques

The practice of the present invention will employ, unless otherwise indicated, conventional techniques of molecular biology, immunology, biochemistry, microbiology, cell biology, genomics, recombinant DNA, which are within one skilled in the art.

Definitions of Terms

The terms used throughout this specification are defined as follows, unless otherwise limited in specific instances.

As used in the specification and the claims, the singular form "a", "an" and "the" include plural references unless the context clearly dictates otherwise. For example, the term "a vector" includes a plurality of vectors, including mixtures thereof.

The terms "polypeptide", "peptide" and "protein" are used interchangeably herein to refer to polymers of amino acids of any length. The polymer may be linear, cyclic, or branched; it may comprise modified amino acids; and it may be interrupted by non-amino acids. The terms also encompass amino acid polymers that have been modified, for example, via glycosylation. As used herein, the term "amino acid" refers to either natural and/or unnatural or synthetic amino acids, including glycine and both the D- and L-optical isomers, and amino acid analogues and peptidomimetics.

Percent identity, in the case of both polypeptides and nucleic acids, may be determined by visual inspection. Percent identity may also be determined using the alignment method of Needleman and Wunsch (J. Mol. Biol., 48:443 (1970)) as revised by Smith and Waterman (Adv. Appl. Math, 2:482 (1981)). In particular, percent identity is determined by using a computer program, for example, the GAP computer program version 10.x available from the Genetics Computer Group (GCG; Madison, Wis., see also Devereux et al., Nucl. Acids Res., 12:387 (1984)). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res., 14:6745 (1986), as described by Schwartz and Dayhoff, eds., Atlas of Protein Sequence and Structure, National Biomedical Research Foundation, 353-358 (1979) for amino acids; (2) a penalty of 30 (amino acids) or 50 (nucleotides) for each gap and an additional 1 (amino acids) or 3 (nucleotides) penalty for each symbol in each gap; (3) no penalty for end gaps; and (4) no maximum penalty for long gaps. Other programs used by one skilled in the art of sequence comparison may also be used.

A "fusion protein" as used herein refers to a protein that contains at least two polypeptides, the first polypeptide of which normally exists as a separate protein and is brought together to form a fusion protein with at least a second polypeptide that is normally not part of the primary structure of the first polypeptide, or that is not arranged in cis configuration with the first polypeptide; or they may normally exist in the same protein but are placed in a new arrangement in the fusion protein. A fusion protein may be created by making and translating a nucleic acid, in vitro or in a host cell, in which the peptide regions are encoded in the desired relationship, or by chemical synthesis, or by both methodologies.

"Oligomerization" of proteins, in particular, a target receptor complex, as used herein refers to an association of separate polypeptides, or subunits or monomers, to form, e.g., a dimer, a trimer, or a tetramer, which may or may not depend on ligand induction. Depending on the nature of the membrane target receptor, the oligomerization of the subunits may be a homo-oligomerization (association of at least two subunits of same type, e.g., as in TNFR1 or p55, which forms a trimer of p55) or hetero-oligomerization, (association of at least two subunits in which at least one is different from the other(s), e.g., as in IL-15 receptor complex, which forms a trimer including IL-15 receptor α subunit, IL-2 receptor β subunit, and IL-2 receptor γ subunit).

The term "linked", "fused" or "fusion" are used interchangeably herein. These terms refer to the joining together of two chemical elements or components by whatever means, including recombinant and/or chemical conjugation means. Although the reading frame of the polypeptides in the fusion protein is made continuous throughout the fused segments, the segments may be physically or spatially separated by, for example, an in-frame linker sequence.

In the context of polypeptide, a "sequence" is an order of amino acids in a polypeptide in an N- to C-terminus direction in which residues that neighbor each other in the sequence are contiguous in the primary structure of the polypeptide.

The terms "nucleic acids" and "polynucleotides", are used interchangeably. They refer to a polymeric form of nucleotides of any length, either deoxyribonucleotides or ribonucleotides, or analogs thereof.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually connotes a suitable host cell comprised of an expression vector that can function to yield a desired expression product.

The term "effective amount" used herein refers to an amount of a polypeptide, e.g., a heterodimeric polypeptide, that will produce the desired biological or physiological effect. As would be known in the art, an effective amount of a therapeutic is required in the methods of treating a disease, a disorder, or a condition, in addition to the prophylactic methods or methods of preventing such diseases, disorders or conditions. Accordingly, with respect to treatment methods, as well as methods of ameliorating a symptom associated with a disease, disorder or condition, an "effective amount" is used synonymously with a "therapeutically effective amount". In such methods, a "subject having a condition" or "subject in need" is any animal, e.g., a human, who exhibits a symptom of, at risk of developing, or diagnosed as having a disease, disorder or condition, in particular, a condition which is mediated by the oligomerization of the target receptors as described in the present disclosure.

The term "Fc", "Fc molecule", "Fc region", or "Fc domain" encompasses native Fc and Fc variant molecules and sequences. Broadly, the term "Fc" is used to define a C-terminal region of an immunoglobulin heavy chain. As with Fc variants and native Fc's, the term "Fc domain" includes molecules in monomeric (e.g. as in the heavy chain or in the light chain part of the fusion protein prior to their interaction with each other to form the heterodimeric polypeptide of the present invention) or multimeric form (e.g., as in the heterodimeric polypeptide of the present invention, or in the full IgG molecule), whether digested from whole antibody or produced by other means. The term "native Fc" refers to molecule or sequence comprising the sequence of a non-antigen-binding fragment resulting from digestion of whole antibody, whether in monomeric or multimeric form. The original immunoglobulin source of the native Fc is, for example, of human origin and may be any of the immunoglobulins, including but not limited to IgG1 and IgG2. Native Fc's are made up of monomeric polypeptides that may be linked into dimeric or multimeric forms by covalent (e.g., disulfide bonds) or non-covalent interaction. The number of intermolecular disulfide bonds between monomeric subunits of native Fc molecules ranges from 1 to 4, depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al., Nucleic Acids Res., 10:4071-4079 (1982)). The term "native Fc" as used herein is generic to the monomeric, dimeric, and multimeric forms. The term "Fc variant" refers to a molecule or sequence that is modified from a native Fc but still comprises a binding site for the salvage receptor, FcRn. WO 97/34631 and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. The term "Fc variant" also comprises a native Fc which comprises a domain which enhances the dimerization of two immunoglobulin chains, for example, the dimerization of the heavy chain and the fusion protein to form the heterodimeric polypeptide of the present invention. Such domains include but are not limited to a free-thio containing compound, e.g., a cysteine residue, and a multimerization domain as described in U.S. Pat. No. 5,807,706 and U.S. Publication No. 2003/0078385, both of which are herein incorporated by reference in their entirety.

The term "hinge region" is generally defined as stretching from $Glu_{216}$ to $Pro_{230}$ of human IgG1 (Burton, Molec. Immunol., 22:161-206 (1985)). Hinge regions of other IgG isotypes may be aligned with the IgG1 sequence by placing the first and last cysteine residues forming inter-heavy chain S—S bonds in the same positions. The hinge region may be of natural occurrence or non-natural occurrence, including but not limited to an altered hinge region as described in U.S. Pat. No. 5,677,425, which is incorporated herein in its entirety. The hinge region may comprise of a complete hinge region derived from an antibody of a different class or subclass from that of the CH1 domain.

The term "tagging moiety" as used herein refers to a polypeptide or a peptide which is fused to the heavy chain of the present invention to help facilitate the separation and/or purification of the heterodimeric polypeptide, which comprises such heavy chain, from the other components in a mixture, e.g., as produced recombinantly, that do not contain the tagging moiety.

The term "antagonize" or "antagonizing" as used herein refers to blocking, impeding, preventing, reducing, inhibiting, lessening or in some way interfering with the biological activity of the associated protein of interest such as a target receptor. The term "antagonist" or "antagonistic" refers to a compound that antagonizes a biological activity of the protein of interest.

The terms "agonize," "agonist" and "agonistic" when used herein refer to or describe a molecule which is capable of, directly or indirectly, substantially inducing, promoting or enhancing cytokine biological activity or cytokine receptor activation.

The term "antibody" is used in the broadest sense and specifically covers monoclonal antibodies (including full length monoclonal antibodies), polyclonal antibodies, monospecific antibodies, multispecific antibodies (e.g., bispecific antibodies), and antibody fragments as long as they still exhibit the desired biological activity. The term "monoclonal antibody" refers to an antibody composition having a homogenous (essentially identical) antibody population. The term is not limited regarding the species, e.g., human, murine, mouse, or came or source of the antibody, nor is it limited by the manner in which it is made. For example, the term includes monoclonal antibodies produced by a methodology other than hybridoma which results in monoclonal antibodies no matter how subcategorized, e.g., hybrid, altered, chimeric, or humanized. Further, the term includes variants that naturally arise during the production of monoclonal antibodies. The term includes whole immunoglobulins. The term "humanized antibody" as used herein refers to an engineered antibody that typically comprises the variable region of a non-human (e.g., murine) antibody, i.e., a chimeric antibody, or at least the complementarity determining regions (CDRs) thereof, and the remaining immunoglobulin portions derived from a human antibody. Procedures for the production of chimeric antibody and further engineered monoclonal antibodies include those described in Riechmann et al., Nature, 332:323 (1988); Liu et al., PNAS, 84:3439 (1987); Larrick et al., Bio/Technology, 7:934 (1989); and Winter and Harris, TIPS, 14:139 (May 1993). Such humanized antibodies may be prepared by known techniques and offer the advantage of reduced immunogenicity when the antibodies are administered to humans.

The phrase "specifically binding" as used herein refers to a binding reaction between an antibody, including the heterodimeric polypeptide of the present invention, and a protein, e.g., a target receptor, which is determinative of the presence of the protein in a heterogeneous population of proteins and other chemical species. Thus, under designated immunoassay conditions, the antibodies bound to a particular protein do not bind in a significant amount to other proteins present in a sample. Specifically binding to a protein under such conditions may require an antibody that is selected for its specificity for that particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York (1988), for a description of immunoassay formats and conditions that could be used to determine selective binding.

Heterodimeric Polypeptides

The heterodimeric polypeptide of the present invention provides a new approach for antagonizing ligand-induced activity of a cytokine receptor or a chemokine receptor, for example, TNF-induced activity of TNFR1 or p55. In particular, the heterodimeric polypeptide encompasses a monovalent IgG, which is comprises a two-chain structure, a heavy chain and a light chain that is further fused to an Fc domain. Thus, compared to the bivalent, four-chain structure of full IgG, this new form of IgG is a two-chain molecule, with only one antigen-binding moiety. The heavy chain of this molecule is the same as in a standard IgG. The light chain, however, is further extended by fusion with sequence from the Fc region of IgG heavy chain. Solely by way of illustration of the present invention and by no means limiting the scope of the present invention, a monovalent IgG directed against mouse TNFR1 was constructed, as described in the Examples section. Based on molecular modeling, the first five residues in the upper hinge region of fusion protein, which is made up of the human IgG light chain and the Fc domain of the human IgG heavy chain (LC/Fc(huIgG1)), were deleted at the juncture between the light chain and Fc to form a symmetrical structure between the two chains beyond the fusion juncture. FIG. 5 Overall the Fc region of this molecule is identical to IgG, and thus it is expected to have similar effector function as the full IgG molecule, including a long serum half-life in vivo.

Figure 2:
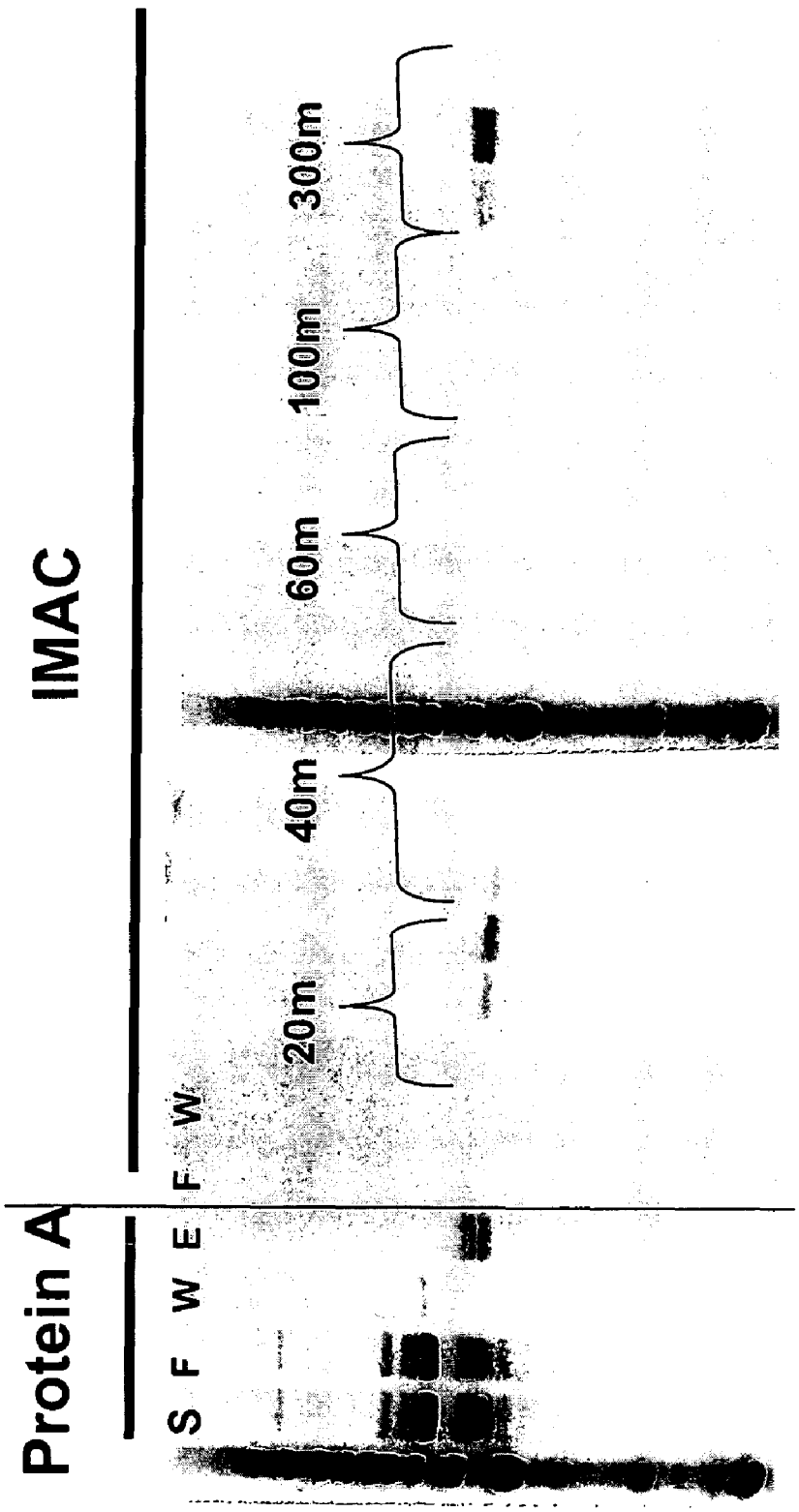
FIG. 2 shows the result of production and purification of 14D2 monovalent IgG in COS cells. Abbreviations: S, supernatant; FT, flow through; W, wash; EL, elute.

The monovalent form of IgG can be made in all four human IgG isotypes, using either κ or λ light chain sequence. The juncture sequence in the light chain construct will be different in human IgG1, IgG2, IgG3, or IgG4 format. As showed in FIG. 1, when the DNA construct encoding the heavy chain and that encoding the fusion protein are introduced into a mammalian cell, only two forms of mature protein products can be secreted from the transfected cells: the two-chain monovalent IgG (i.e., the heterodimeric polypeptide) and the fusion protein homodimer. The heavy chain homodimer cannot be secreted because it lacks the light chain. The resulting heterodimeric polypeptide can be separated from the fusion protein dimer by affinity chromatography using a peptide tag, e.g. His tag, which is present on the heavy chain construct, as shown in FIG. 2.

Other variations can be designed, especially in the linker/hinge region connecting the Fab and Fc segments of the molecule. Length variations (both longer and shorter than the linkers described here) in both the heavy chain linker sequence and light chain-Fc fusion chain linker sequence would be predicted to result in molecules having altered properties, some which may have a profound influence on the pharmacokinetic behavior of the therapeutic molecule in vivo.

Uses

In general, the present invention also provides methods of using the heterodimeric polypeptide for treating or preventing a disorder or a disease, which may be used in in vitro, ex vivo and in vivo. The diseases contemplated to be treated with the present invention include, but are not limited to, those which is at least mediated by activation of at least one member of the TNF/TNF receptor super family is involved, for example, TNFR1 (p55) or TNFR2 (p75). These diseases include, but are not limited to, autoimmune disease. As used herein, autoimmune disease describes a disease state or syndrome whereby a subject's body produces a dysfunctional immune response against the subject's own body components, with adverse effects. This may include production of B cells which produce antibodies with specificity for all antigens, allergens or major histocompatibility (MHC) antigens, or it may include production of T cells bearing receptors that recognize self-components and produce cytokines that cause inflammation. Examples of autoimmune diseases include, but are not limited to, ulcerative colitis, Crohn's disease, multiple sclerosis, rheumatoid arthritis, diabetes mellitus, pernicious anemia, autoimmune gastritis, psoriasis, Bechet's disease, Wegener's granulomatosis, Sarcoidois, autoimmune thyroiditis, autoimmune oophoritis, bullous pemphigoid, phemphigus, polyendocrinopathies, Still's disease, Lambert-Eaton myasthenia syndrome, myasthenia gravis, Goodpasture's syndrome, autoimmune orchitis, autoimmune uveitis, systemic lupus erythematosus, Sjogren's Syndrome and ankylosing spondylitis.

Furthermore, the target receptors against which the heterodimeric polypeptide of the present invention can be used include those which are activated by the oligomerization of their subunits. Thus, the target receptors contemplated by the present invention include but not limited to TNF/TNF receptor superfamily, e.g., including those described in Locksley et al., Cell, 104:487-501 (2001), receptor tyrosine kinases, e.g., including those described in Schlessinger, Cell, 103:211-225 (2000), G-protein coupled receptors (GPCRs), e.g., including those described in Pin et al., FEBS Journal, 272:2947-2955 (2005), Fc receptors (FcRs), e.g., including those described in Hogarth, Current Opinion in Immunology, 14:798-802 (2002), AT1 receptors, e.g., including those described in Dechend et al., Semin. Nephrology, 24:571-579 (2004), tissue factors, e.g., including those described in Houston, Expert Opin. Ther. Targets, 6:159-174 (2002), and integrins, e.g., including those described in Li et al., Science, 300:795-798 (2003).

Pharmaceutical Compositions

Pharmaceutical compositions of the present invention may be made for administration by injection, oral, pulmonary, nasal, transdermal or other forms of administration. In general, the invention encompasses pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th ed., Mack Publishing Co., Easton, Pa. 18042, 1435-1712 (1990), which are herein incorporated by reference. The compositions may be prepared in liquid form, or may be in dried powder, such as lyophilized form. Implantable sustained release formulations are also contemplated, as are transdermal formulations.

Contemplated for use herein are oral solid dosage forms, which are described generally in Chapter 89 of Remington's Pharmaceutical Sciences, 18th ed., Mack Publishing Co., Easton Pa. 18042 (1990), which is herein incorporated by reference. Solid dosage forms include tablets, capsules, pills, troches or lozenges, cachets or pellets. Also, liposomal or proteinoid encapsulation may be used to formulate the present compositions as, for example, proteinoid microspheres reported in U.S. Pat. No. 4,925,673. Liposomal encapsulation may be used and the liposomes may be derivatized with various polymers (e.g., U.S. Pat. No. 5,013,556). A description of possible solid dosage forms for the therapeutic is given in Chapter 10 of Marshall, K., Modern Pharmaceutics, G. S. Banker and C. T. Rhodes, eds. (1979), herein incorporated by reference. In general, the formulation will include the inventive compound, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where the moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis, Soluble Polymer-Enzyme Adducts, Enzymes as Drugs, Hocenberg and Roberts, eds., Wiley-Interscience, New York, N.Y., 367-383 (1981); Newmark, et al., J. Appl. Biochem., 4:185-189 (1982). Other polymers that could be used are poly-1,3-dioxolane and poly-1,3,6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl]amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resin. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film-coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary delivery forms. Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharma. Res., 7: 565-569 (1990); Adjei et al., Int'l. J. Pharmaceutics, 63:135-144 (1990), leuprolide acetate; Braquet et al., J. Cardiovasc. Pharmacol., 13(5):s 143-146 (1990) endothelin-1; Hubbard et al., Annals Int. Med., 3:206-212 (1989) alpha.1-antitrypsin; Smith et al., J. Clin. Invest., 84:1145-1146 (1989) alpha.1-proteinase; Oswein et al., "Aerosolization of Proteins", Proc. Symp. Resp. Drug Delivery II, Keystone, Colo. (March 1990) recombinant human growth hormone; Debs et al., J. Immunol., 140:3482-3488 (1988) interferon-.gamma. and tumor necrosis factor alpha; and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to, nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 .μm (or microns), most preferably 0.5 to 5 .μm, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts, which facilitate dispersal of the powder from the device, e.g., 50 to 90% by weight of the formulation.

Nasal delivery forms. Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Buccal delivery forms. Buccal delivery of the inventive compound is also contemplated. Buccal delivery formulations are known in the art for use with peptides.

Dosages

The dosage regimen involved in a method for treating the above-described conditions will be determined by the attending physician, considering various factors which modify the action of drugs, e.g., the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

Other aspects and advantages of the present invention will be further understood upon consideration of the following illustrative examples.

EXAMPLES

Construction of Anti-p55 Monovalent Antibody

A hamster anti-p55TNFR antibody, designated as 14D2, was generated using the mouse p55TNFR as immunogen. The variable heavy chain ($V_H$) and the variable light chain ($V_L$) were cloned from total RNA obtained from the 14D2 hybridoma cells using degenerate primers to the 5'-end sequence, which was deduced from the N-terminal sequence of purified 14D2 as determined by Edman analysis, and 3' primers complementary to sequence encoding the CH1 domain of the hamster IgG1's heavy chain. The 14D2 $V_L$-hu light chain K fusion was made by amplifying the 14D2 $V_L$ with the following primers:

```
5'-CTGGTGCTAGCGATATAGTGATGTCGCAG    (SEQ ID NO: 1)
and

5'-CAGCCACCGTACGTTTGATTTCCAGCTTGG.  (SEQ ID NO: 2)
```

The amplicon was subcloned into a vector containing the sequence of the hu K light chain constant sequence. The 14D2$V_L$-hu κLC-huIgG1Fc fusion was spliced together by overlap extension using the following primers:

```
                                    (SEQ ID NO: 3)
    5'-CGTTTAAACGTCGACGTTTAAACGCCGCCAG;

(SEQ ID NO: 4)
    5'-GGCATGTGTGAGTTTTGTCACACTCTCCCCTGTTG;

(SEQ ID NO: 5)
    5'-CAACAGGGGAGAGTGTGACAAAACTCACACATGCC;
    and (SEQ ID NO: 6)
    5'-GTTTAAACAGATCCGCGGCCGCTCTAGCCCC;
``` and templates: 14D2$V_L$-hu κ LC and hu IgG1.

The 14D2$V_H$-huIgG1-His$_6$ fusion was constructed by amplification of the 14D2 $V_H$ with the following primers, to add AscI and NheI restriction sites 5' and 3', respectively:

```
                                    (SEQ ID NO: 7)
    5'-GAG GGC GCG CCG AAG TGC AGC TGG TGG AG;
    and (SEQ ID NO: 8)
    5'-GGT GCT AGC TAA AGA GAC GGT GAC CAG AG
``` to ligate the 14D2$V_H$ directly upstream to the huIgG1-His$_6$ constant sequence in a mammalian expression vector.

Production of Anti-p55 Monovalent Antibody

COS-PKB cells were transfected simultaneously with expression plasmids containing the 14D2$V_H$-huIgG1-His$_6$ fusion protein (SEQ ID NO: 9), and the 14D2V$_L$-hu κLC-huIgG1Fc fusion protein (SEQ ID NO: 10), by DEAE-dextran method. Cells were then incubated at 34° C., 10% $CO_2$ in low IgG medium (0.5%). Cell culture supernatants were harvested on day 7 post-transfection.

Polypeptide Purification

Cell culture supernatants were filtered through a 0.2μ filter. The filtered supernatants were applied to a HiTRAP rProtein A FF column (Amersham). Protein was eluted by 100 mM glycine pH 2.7/150 mM NaCl. The eluent was dialyzed v. PBS and further purified by metal chelation using a HisTRAP HP kit (Amersham) as follows: apply dialyzed sample to HisTrap column, precharged with Ni$^+$, wash column with PBS, elute with a step gradient of imidazole (20, 40, 60, 100, 300, 500 nM). Collect peak fractions and dialyze against PBS. Results are shown in FIG. 2.

Western Blot

Figures 3A, 3B:
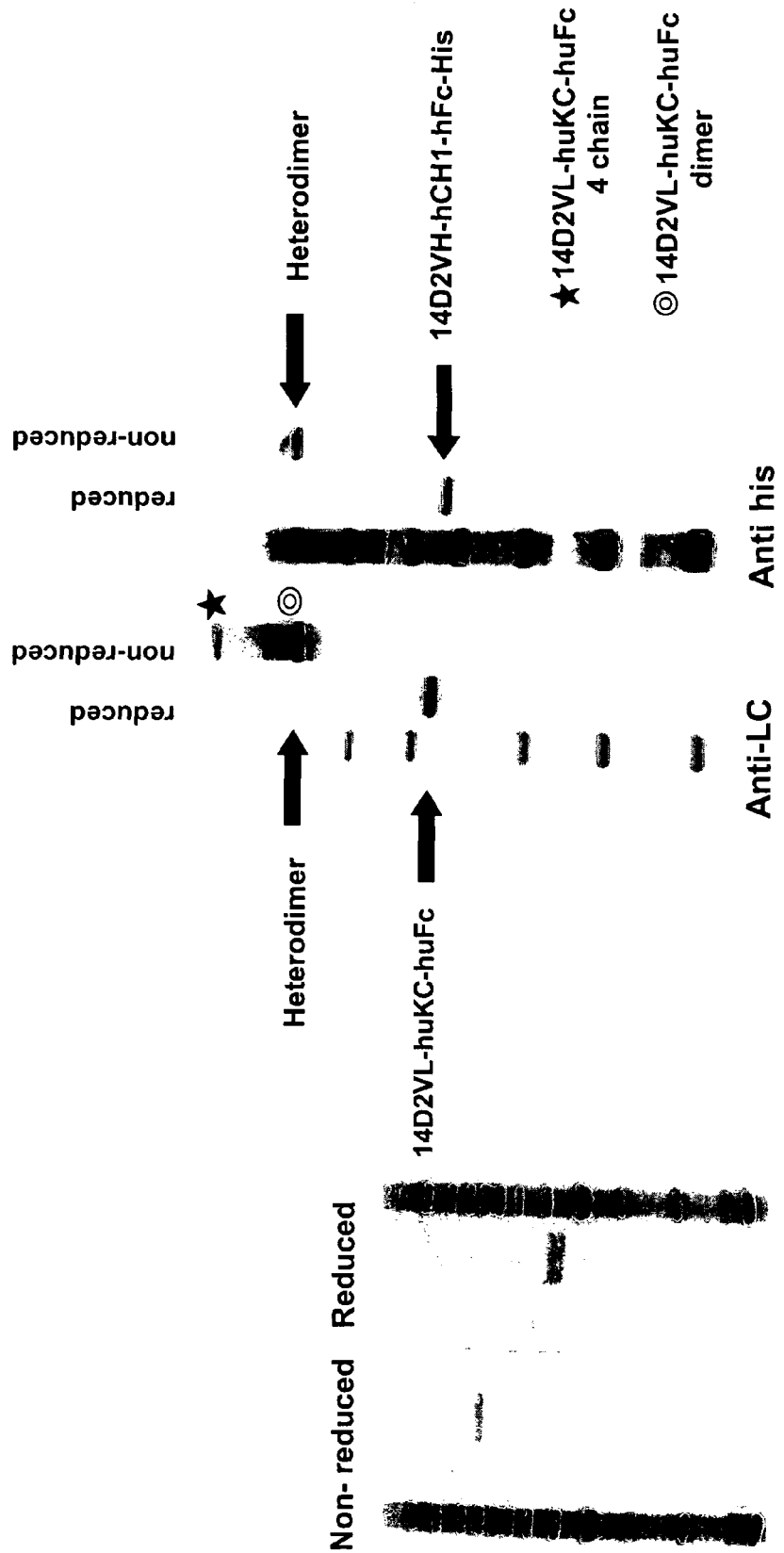
FIG. 3A shows molecular characterization of monovalent IgG in 300 mM imidazole fractions. SDS-PAGE analysis of the 300 mM imidazone fraction under reduced and non-reduced conditions.
FIG. 3B shows molecular characterization of monovalent IgG by Western Blot of the 300 mM imidazole fraction using an anti-light chain-HRP antibody (left) and an anti-polyHis-HRP antibody (right). The molecular content of each band was highlighted by the arrows.

The eluted polypeptides from 500 nM imidozole fraction were analyzed on SDS-PAGE gel under reduced and non-reduced conditions, then transferred to nylon membrane and subjected to Western blot using HRP conjugated anti-polyhistidine antibody (Sigma A 7058) or goat anti-human kappa light chain antibody (Sigma A7164). Results are shown in FIGS. 3A and 3B.

L929 Assays

Figure 4:
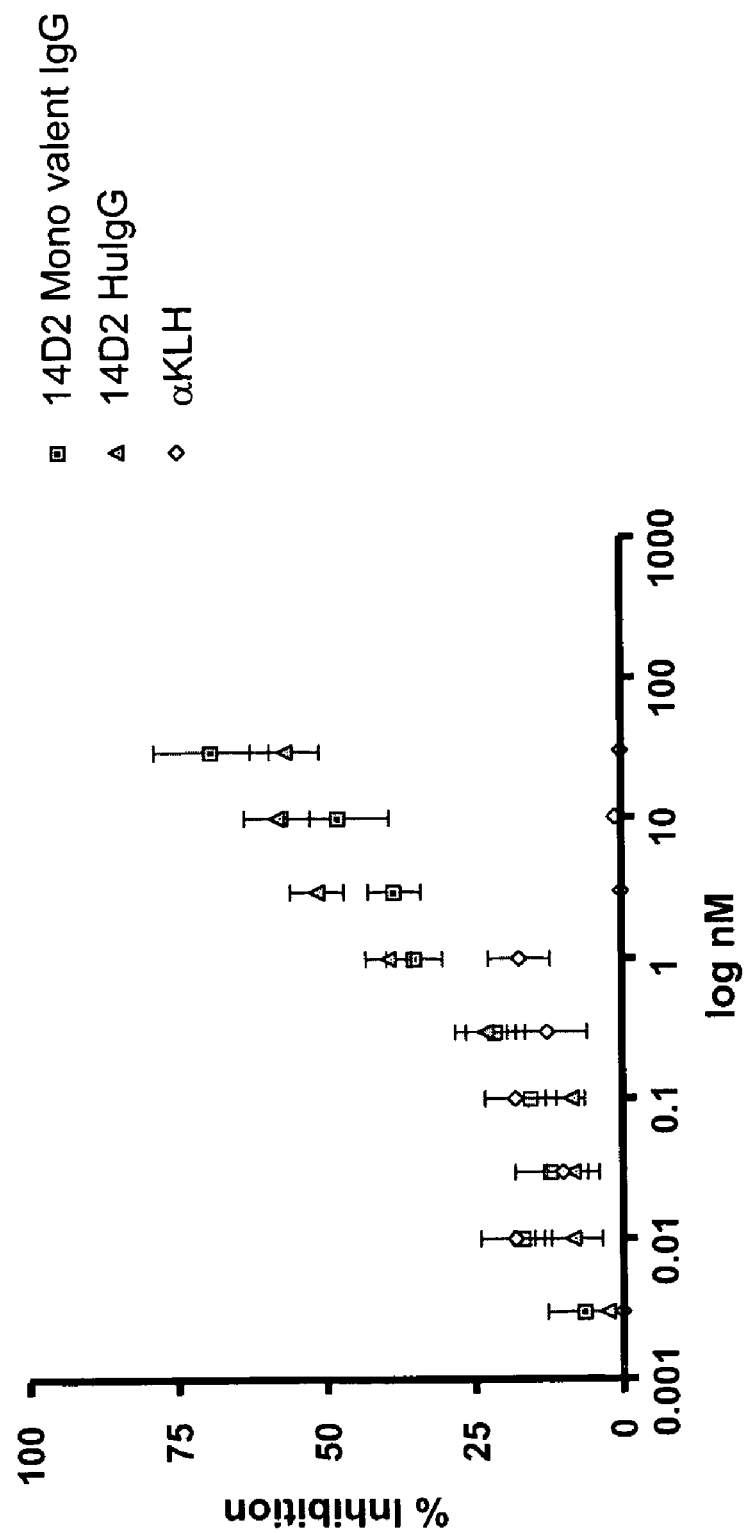
FIG. 4 shows the result of an TNF mediated cytolytic assay using L929 cells. 14D2 anti-mouse p55TNFR antibody was reformatted as monovalent IgG1 and hamster-human IgG1 chimera. Both antibodies were tested for their ability to block TNF mediated cell killings in L929 cells. Anti-KLH antibody was used as a control.

The biological activity of the anti-p55 monovalent antibody described above was tested in cytolytic assays using mouse L929 cell targets, murine or human TNF as cytotoxic agents. Death was assessed by the crystal violet indicator (Mohler et al., J. Immunology, 151(3):1548-1561 (1993)). Briefly, $2×10^4$ L929 cells were plated in 96-well trays (Costar) in a total volume of 100 μl media and incubated overnight at 37° C. in 5% $CO_2$ atmosphere. Spent media was then removed, and media containing 1 ng/ml μTNF, in the presence or absence of serial dilutions of the antibody, was added. Actinomycin D (5 mg/ml) was present in all wells. The constant amount of 1 ng/ml TNF, which produced 100% cytolysis in this assay, was determined from previous experiments. After 12 hours of incubation, cells were washed with PBS and stained for 10 min with 100 ml of 0.5% crystal violet in methanol/water (1/4). Plates were washed with distilled water, and the indicator was solubilized with 2% sodium deoxycholate. All assays were performed in triplicate. Absorbance (A) at 570-630 nm was determined in a microplate reader (Molecular Devices, Palo Alto, Calif.). Results are shown in FIG. 4.

---

What is claimed is:

1. A heterodimeric polypeptide comprising
   (a) a human or humanized IgG1, IgG2, or IgG4 heavy chain from an antibody that binds specifically to an antigen and that comprises an Fe region, wherein the heavy chain comprises a heavy chain variable ($V_H$) region, followed by a first heavy chain constant ($C_H1$) region, followed by a hinge region, followed by a second heavy chain constant ($C_H2$) region, followed by a third heavy chain constant ($C_H3$) region, and
   (b) a fusion protein, wherein the fusion protein comprises a light chain from the antibody followed by a human IgG1, IgG2, or IgG4 Fe molecule, wherein the light chain comprises a light chain variable ($V_L$) region followed by a light chain constant ($C_L$) region and wherein the human IgG1, IgG2, or IgG4 Fe molecule comprises a hinge region followed by a $C_H 2$ region followed by a $C_H 3$ region, wherein
      (i) the first five amino acids of the hinge region of the fusion protein are deleted, or
      (ii) the hinge region of the fusion protein is not shortened or lengthened,
   wherein the heavy chain and the fusion protein are two polypeptide chains that are oriented identically with respect to their N- and C-termini and associate to form the heterodimeric polypeptide,
   wherein the heterodimeric polypeptide is monovalent, and wherein the heterodimeric polypeptide is capable of specifically binding to the antigen.

2. The heterodimeric polypeptide of claim 1, wherein the heavy chain and the fusion protein are not mutated in their CH3 regions.

3. The heterodimeric polypeptide of claim 1, wherein the heavy chain and the fusion protein are mutated in their CH3 regions so as to form multimerization domains.

4. The heterodimeric polypeptide of claim 3, wherein the mutations are substitutions.

5. The heterodimeric polypeptide of claim 1, wherein the light chain is a kappa light chain.

6. The hoterodimeric polypeptide of claim 1, wherein the light chain is a lambda light chain.

7. The heterodimeric polypeptide of claim 1, wherein the antibody is a human antibody.

8. The heterodimeric polypeptide of claim 1, wherein the antibody is a humanized antibody.

9. The heterodimeric polypeptide of claim 1, wherein the heavy chain and the fusion protein are covalently linked.

10. The heterodimeric polypeptide of claim 9, wherein the covalent linkage is a disulfide bond.

11. The heterodimeric polypeptide of claim 1, wherein the hinge region of the fusion protein is not shortened or lengthened.

12. The heterodimeric polypeptide of claim 1, wherein the first five amino acids of the binge region of the fusion protein are deleted.

13. The heterodimeric polypeptide of claim 1, wherein the heavy chain further comprises a tagging moiety.

14. The heterodimeric polypeptide of claim 13, wherein the tagging moiety is selected from the group consisting of: hexa-histidine tag, streptavidin-binding peptide, maltose-binding protein, glutathione S-transferase, mic-tag, and FLAG-tag.

15. The heterodimeric polypeptide of claim 14, wherein the tagging moiety comprises a hexa-histidine tag.

16. The heterodimeric polypeptide according to claim 1, wherein the sequences of the hinge region are naturally occurring sequences.

17. The heterodimeric polypeptide of claim 1, wherein the heavy chain and the lusion protein contain no cysteine residues that are unpaired.

18. The heterodimeric polypeptide of claim 12, wherein the Fe region of the heavy chain and the Fe molecule of the fusion protein are of the IgG1 isotype.

19. The heterodimeric polypeptide of claim 11, wherein the Fe region of the heavy chain and the Fe molecule of the fusion protein are of the IgG2 isotype.

20. The heterodimerie polypeptide of claim 11, wherein the Fe region of the heavy chain and the Fe molecule of the fusion protein are of the IgG4 isotype.

21. The heterodimeric polypeptide of claim 1, wherein the antigen is a receptor which is activated by the oligoimerization of its subunits.

22. The heterodimeric polypeptide of claim 21, which antagonizes the activity of the receptor.

23. The heterodimeric polypeptide of claim 21, wherein the oligomerization forms an oligomer which is at least a dimer.

24. The heterodimeric polypeptide of claim 23, wherein the oligomerizatim forms an oligomer which is at least a trimer.

25. The heterodimeric polypeptide of claim 24, wherein the oligomerization forms an oligomer which is at least a tetramer.

26. The heterodimeric polypeptide of claim 21, wherein the receptor is a member of a family selected from the group consisting of: TNF/TNF receptor superfamily, cytokine receptors, receptor tyrosine kinases, G-protein coupled receptors (GPCRs), Fe receptors (FeRs), AT1 receptors, tissue factors, and integrins.

27. The heterodimeric polypeptide of claim 26, wherein the receptor is a member of the TNF/TNF receptor superfamily.

28. The heterodimeric of claim 27, wherein the member is selected from the group consisting of: TNFR1, TNFR2, NGFR, Troy, EDAR, XEDAR, CD40, DeR3, Fas, OX40, AITR, CD30,HveA, 4-1BB, DR3, CD27, LTβR, RANK, TWEAK receptor, TACI, BCMA, DR6, OPG, DR4, DR5, DeR1 and DeR2.

29. The heterodimeric polypeptide of claim 26, wherein the receptor is a receptor tyrosine kinase.

30. The heterodimeric polypeptide of claim 29, wherein the receptor tyrosine kinase is selected from the group consisting of: growth hormone receptor, erythropoietin receptor, VEGF receptor, FGF receptor, PFGF receptor and EGF receptor.

31. The heterodimeric polypeptide of claim 30, wherein the receptor tyrosine kinase is an EGF receptor selected from the group consisting of ErbB1, ErbB2, ErbB3 and ErbB4.

32. The heterodimeric polypeptide of claim 26, wherein the receptor is an interleukin receptor.

33. The heterodimeric polypeptide of claim 32, wherein the interleukin receptor is a receptor of an interleukin selected from the group consisting of: IL-1, IL-2, IL-4, IL-15, IL7, TSLP, LIF, IL-13, IL-23 and IL-31.

34. The heterodimeric polypeptide of claim 21, which does not agonize the activity of the receptor.

35. The heterodimeric polypeptide of claim 1, wherein the heavy chain comprises CDRs having the amino acid sequences of SEQ ID NOS: 11, 12 and 13, and the light chain comprises CDRs having the amino acid sequences of SEQ ID NOS:18, 19 and 20 and wherein the heterodimeric polypeptide is capable of binding to and inhibiting the activity of TNFR1.

36. The heterodimeric polypeptide of claim 1, wherein the heavy chain and the fusion protein form a symmetrical structure beyond the fusion juncture of the fusion protein.

37. The heterudimeric polypeptide of claim 3, wherein the heavy chain and the fusion protein are mutated at one or more interface amino acid residues in their CH3 regions.

38. The heterodimeric polypeptide of claim 3, wherein the heavy chain and the fusion protein are mutated at one or more contact amino acid residues in their CH3 regions.

39. A. composition comprising the heterodimeric polypeptide of claim 1 and a pharmaceutically acceptable carrier.

40. An isolated heterodimeric polypeptide comprising a first polypeptide comprising the amino acid sequence set forth in SEQ ID NO:9 and a second polypeptide comprising the amino acid sequence set forth in SEQ ID NO:10.

* * * * *